(12) United States Patent
Schmid et al.

(10) Patent No.: US 7,284,981 B2
(45) Date of Patent: Oct. 23, 2007

(54) FUNCTIONAL HANDPIECE HAVING A LIGHT EMISSION ELEMENT AT ITS FORWARD END

(75) Inventors: Gerhard Schmid, Mittelbiberach (DE); Franz Liebhardt, Ochsenhausen (DE); Gerd Löhn, Biberach-Rissegg (DE); Hubert Mösslang, Oberdischingen (DE)

(73) Assignee: Kaltenbach & Voigt GmbH & Co. KG, Biberach (DE)

( * ) Notice: Subject to any disclaimer, the term of this patent is extended or adjusted under 35 U.S.C. 154(b) by 466 days.

(21) Appl. No.: 10/643,709

(22) Filed: Aug. 19, 2003

(65) Prior Publication Data
US 2004/0076922 A1 Apr. 22, 2004

(30) Foreign Application Priority Data
Aug. 22, 2002 (DE) ................. 102 38 555

(51) Int. Cl.
*A61C 3/00* (2006.01)
*A61C 17/02* (2006.01)
*F21V 33/00* (2006.01)
*B25B 23/18* (2006.01)
*A61B 18/18* (2006.01)

(52) U.S. Cl. .................. 433/29; 433/80; 433/126; 606/2; 362/109; 362/119

(58) Field of Classification Search ............. 433/29, 433/80, 126; 602/2–26; 362/109–120, 555–582
See application file for complete search history.

(56) References Cited

U.S. PATENT DOCUMENTS 1,355,659 A * 10/1920 Evslin ................. 192/69.7
3,109,238 A * 11/1963 Marks ................. 433/131

(Continued)

FOREIGN PATENT DOCUMENTS

DE 33 37 166 A1 4/1985

(Continued)

*Primary Examiner*—John J Wilson
(74) *Attorney, Agent, or Firm*—Marshall Gerstein & Borun LLP

(57) ABSTRACT

Functional handpiece 1 having an elongate handpiece body which has at its rearward end a connection element for connection with a flexible supply line, and has at its forward end a light emission element of a light permeable material for the illumination of the treatment site, and has in the light emission element an outlet opening for a medium such as water or air or spray, the light emission element forming a forward region of the functional handpiece and being releasably connected with the remaining region of the functional handpiece, and the light emission element having a plug-in fitting for the light emission element. In order to improve the functional handpiece with the regard to the illumination of the treatment site, the light emission element is connected with the remaining region of the functional handpiece by means of a latching device, the latching device having a latching nose directly or indirectly arranged on the light emission element, which can spring in radially inwardly and can self-actingly spring out behind a latching edge on the plug-in fitting.

16 Claims, 3 Drawing Sheets

U.S. PATENT DOCUMENTS

| | | | | |
|---|---|---|---|---|
| 3,510,643 A | * | 5/1970 | File | 362/26 |
| 3,815,240 A | | 6/1974 | Loge | 433/126 |
| 3,889,661 A | * | 6/1975 | Fiore | 600/184 |
| 4,332,562 A | * | 6/1982 | Schuss et al. | 433/126 |
| 4,619,612 A | | 10/1986 | Weber et al. | 433/80 |
| 4,648,838 A | | 3/1987 | Schlachter | 433/29 |
| 4,807,599 A | * | 2/1989 | Robinson et al. | 600/212 |
| 5,352,221 A | * | 10/1994 | Fumich | 606/15 |
| 5,899,692 A | * | 5/1999 | Davis et al. | 433/80 |
| 5,931,670 A | | 8/1999 | Davis | 433/91 |
| 6,208,788 B1 | * | 3/2001 | Nosov | 385/121 |
| 6,325,623 B1 | * | 12/2001 | Melnyk et al. | 433/29 |

FOREIGN PATENT DOCUMENTS

| | | |
|---|---|---|
| DE | 35 00 085 C2 | 7/1986 |
| DE | 100 45 115 A1 | 3/2002 |
| WO | WO99/47068 | 9/1999 |
| WO | WO 01/82825 | 11/2001 |

* cited by examiner

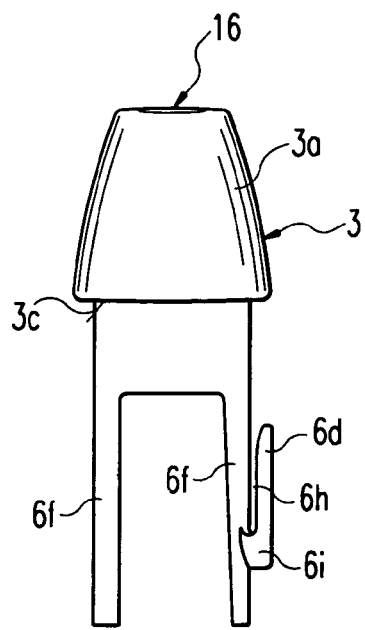
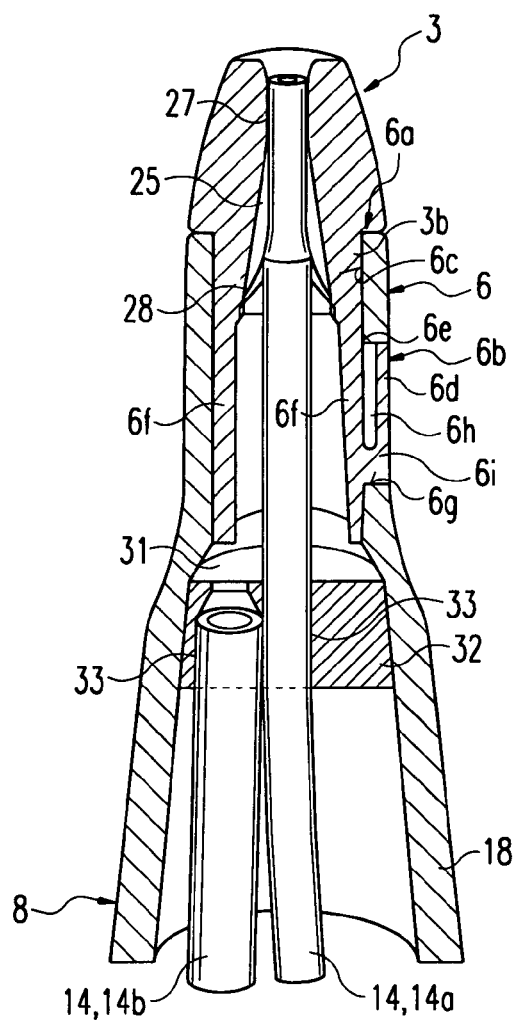

FUNCTIONAL HANDPIECE HAVING A LIGHT EMISSION ELEMENT AT ITS FORWARD END

BACKGROUND OF THE INVENTION

1. Field of the Invention

The invention relates to a functional handpiece.

2. Description of Related Technology

With medical or dental handpieces one distinguishes between those which are equipped or can be equipped with a tool for the treatment of the human or animal body and with which the human or animal body is mechanically acted upon, and those handpieces which serve to keep the treatment site of the human or animal body in a condition which is capable being operated upon, for example delivering water and/or air for cooling and cleaning the treatment site, or delivering light to the treatment site or to remove body fluid, e.g. saliva or blood, from the treatment site, or to probe the treatment site. In the medical field concerned here, the first kind of handpiece are called working handpieces and the second kind functional handpieces. A functional handpiece can thus be a rinsing and/or blowing handpiece, an illumination handpiece or a probe handpiece.

A functional handpiece in the form of a rinsing or blowing handpiece is e.g. described in DE 35 00 085 C2. This dental functional handpiece serves to deliver water and/or air or light to the treatment site. This functional handpiece has an elongate grip part with the forward end of which a cannula is releasably connected which has at its forward end a light emission element to which light can be delivered via a light conductor or directly by a lamp, and which in functional operation emits the light forwardly onto the treatment site. The light emission element is surrounded by a protective tube of the cannula and has at its free end a central nozzle for water and surrounding the nozzle a second annular nozzle for air, which open into a common nozzle hole. The nozzle hole is surrounded by a sleeve which is fixedly placed in a forward receiving hole of the light emission body. The light emission element thus has at its forward end an annular end face out of which the light emerges in an annular form forwardly.

DE 100 45 115 A1 shows a dental or dental-medical handpiece the forward end region of which is formed by a light emission element, which is releasably connected with the handpiece by means of a plug-in fitting with a clamping connection.

From WO 99/47068 A there is described a suction handpiece in a multiplicity of exemplary forms. FIGS. 15 to 19 show a light emission element which is releasably connected with the suction handpiece by means of a plug-in fitting having a latching device.

The forms of treatment of the human or animal body may be of many kinds both with the functional handpiece itself and also together with a further working handpiece, whereby a good illumination of the treatment site is desired so that the person carrying out the treatment can clearly observe both the treatment site itself and also the result of treatment.

SUMMARY OF THE INVENTION

Thus, the object of the invention is to improve a functional handpiece of the kind indicated in the introduction with regard to the illumination of the treatment site. In particular there is to be made possible an increased spatial illumination of the treatment site.

With one embodiment of a multi-function handpiece in accordance with the invention, which is delimited with reference to DE 100 45 115 A, and with a functional handpiece in accordance with another embodiment of the invention, which is delimited with reference to WO 99/47068 A, the light emission element forms the forward end region of the handpiece and it is releasably connected. Here, the improved spatial illumination of the treatment site which is striven for is attained in that in functional operation the light is emitted not only forwardly but also to the side and thus the treatment site is spatially illuminated, whereby due to the considerable size of the light emission element shadow formation is substantially reduced. The releasable connection of the light emission element makes it possible for example to exchange this after its light emission has been impaired, so that the functional handpiece can be maintained in a good functional condition in a time saving and material saving manner. In the case of an impairment of the light emission, which for example is present if the light emission surface is scratched, the light emission element can be exchanged for a new light emission element, so that the exchange can be dealt with with slight outlay in terms of time and material. The releasable connection is preferably a quick-release connection, in particular having a latching device, which makes possible not only a quick connection but also a secure and captive connection.

The light can be delivered to the light emission body through one or two light conductors extending from the rear forwardly, which is or are preferably arranged eccentrically, so that a water line can be so arranged that it is coaxially connected to the light emission element or passes through this coaxially.

The configuration in accordance with the invention is thus suited in advantageous manner for rinsing or spray and blowing handpieces, or the like, or suction handpieces or probe handpieces having an imaging arrangement for the taking of images of the treatment site.

The invention may provide features which improve the accessability of the functional handpiece to the treatment site, provide for small and economically producible configurations and ensure reliable functioning and good handling.

In DE 33 37 166 A1 there is described a dental spray handpiece having a cannula which is releasably connected with the handpiece body by means of a so-called plug-in/turn coupling. The cannula is at least in the rearward region formed solid, whereby a cannula base having the coupling element is formed in one piece with the cannula jacket. Through this, although the cannula is stable, it is intensive in terms of use of material and of relatively heavy construction, which should be avoided.

Thus, the invention further has the object of so configuring a cannula that it is stable whilst maintaining a construction which saves on material and is light.

With this cannula, the cannula base and the cannula jacket are formed in two parts. Further, the cannula base is extended forwardly with a support arm which at a forwardly directed spacing from the cannula base constitutes a transversely directed support between these parts.

Due to the two-part nature, the cannula can be produced in a simple manner to be hollow and thin walled, through which the use of materials and the weight can be reduced.

Despite this, the cannula in accordance with the invention is stable, because the cannula sleeve is laterally supported by means of the support arm which is formed by means of a forwardly directed extension of the cannula base.

This configuration in accordance with the invention is suitable both for cannulas which are straight and also those which are angled to the side or curved to the side. In the case in which at least one media line extends through the cannula it is advantageous to form the support arm with a one-sided wall or in the form of a shell, through which a hollow space is created in which the at least one media line finds room. With a curved or angled cannula, the side wall is preferably arranged on the inner side of the curve or angle.

For connecting the cannula base with the support arm there may be provided a plug-in connection with a plug-in recess, which receives a plug-in pin of the respective plug-in connection part.

BRIEF DESCRIPTION OF THE DRAWINGS

Below, advantageous configurations of the invention will be described in more detail with reference to preferred embodiments. There is shown:

FIG. 3 the forward end region of the cannula, in a further illustration to an enlarged scale;

FIG. 4 a light emission part of the multi-functional handpiece, as an individual part, in a side view.

DETAILED DESCRIPTION

Figure 1:
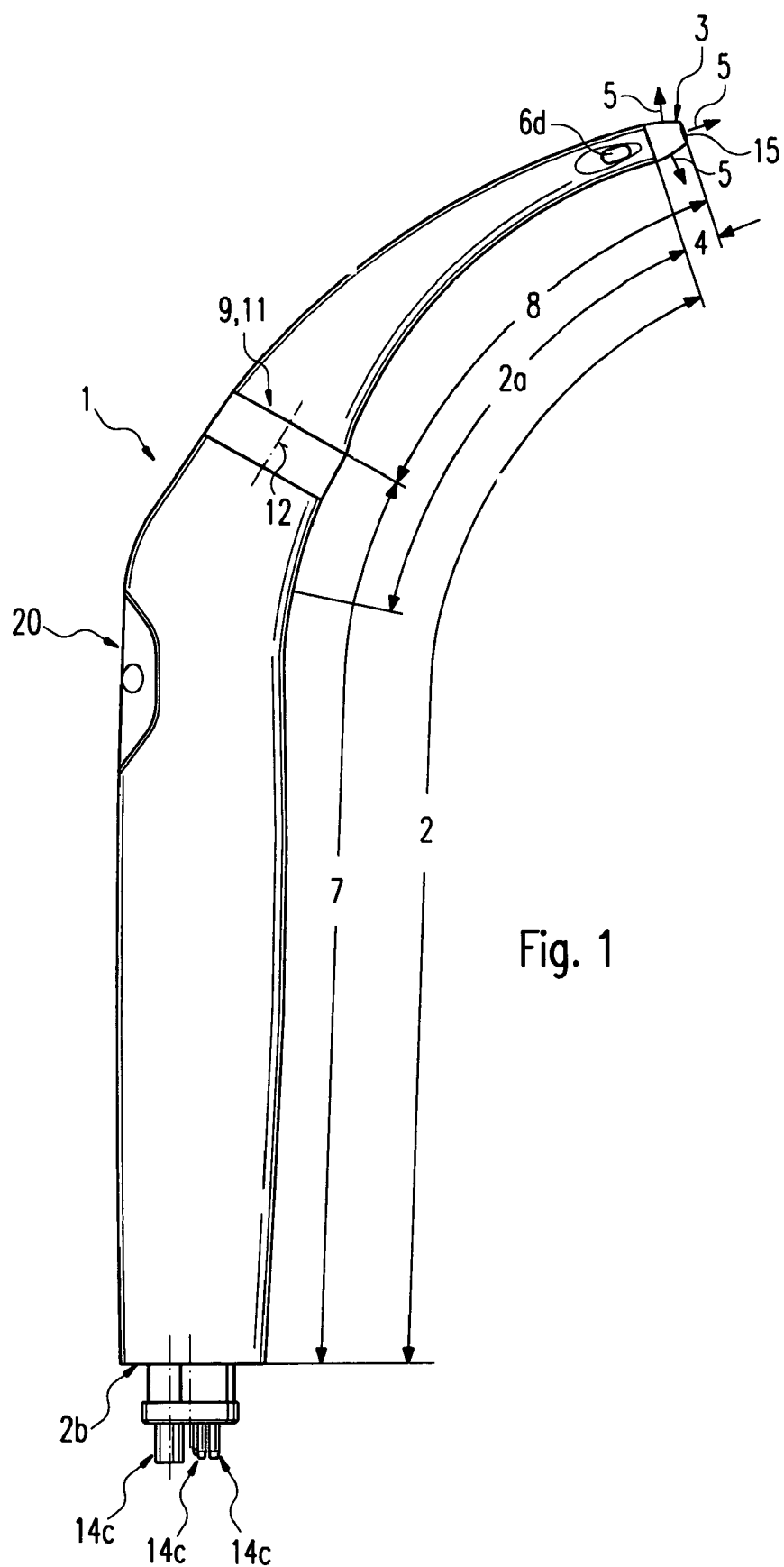
FIG. 1 a multi-functional handpiece in accordance with the invention, in a side view.
Figure 2:
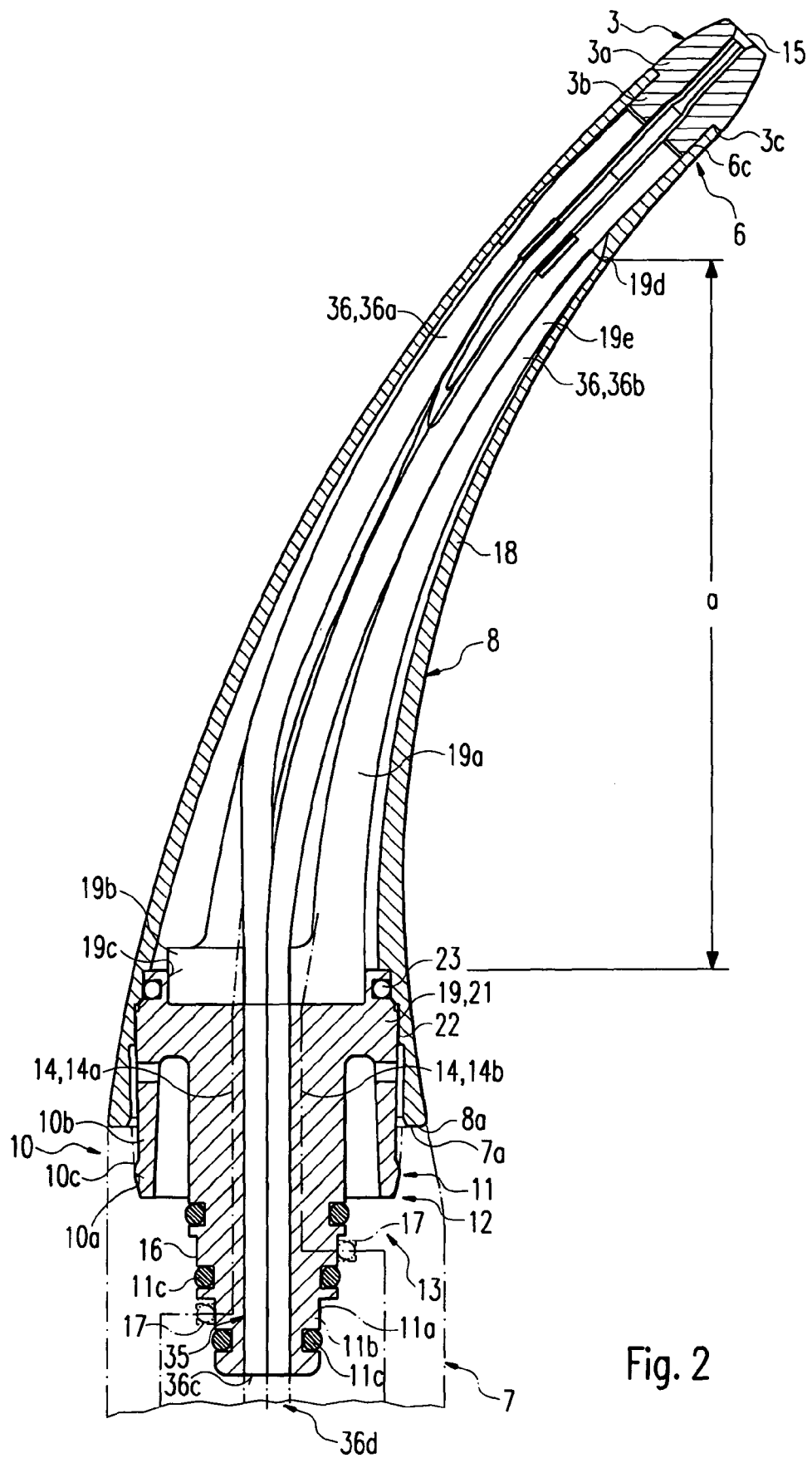
FIG. 2 a cannula of the multi-functional handpiece, in axial section and illustrated to an enlarged scale.

In the case of the present exemplary embodiment, the functional handpiece, designated in its entirety by 1, serves to deliver one or more treatment media, here water and/or air or spray and/or light to a treatment site which is to be treated with the functional handpiece 1. The functional handpiece 1 is of elongate structure and has a handpiece body 2 which may extend straight or may have a forward handpiece section 2a which is angled or curved to the side with its forward end, as the exemplary embodiment shows. From the forward end of the handpiece body 2 there extends a light emission element 3 forwardly, which forms a head section 4 of the functional handpiece 1 and in functional operation emits light forwardly and to all sides, emphasized by light rays 5, and due to the emission surface of considerable size illuminates the treatment site largely free of shadows, which applies at least for the near vicinity of the light emission element 3. In the exemplary embodiment, the light emission element 3 is of plastics or glass or quartz and it has, in one piece, a light emission body 3a forming the head section 4 and a connection body 3b which in the case of the exemplary embodiment is formed by a plug-in pin extending rearwardly centrally from the light emission body 3a. The head section 4 or light emission body 3a bears with a shoulder surface 3c, tapering the connection body 3b, on the forward end of the handpiece body 2.

The connection body 3b is part of a connection device 6 which is preferably formed by means of quick-release device, in particular a plug-in fitting 6a with a latching device 6b which will be described in more detail below. The pin-like connection body 3b is inserted into a matching plug-in recess 6c in the handpiece body 2, which recess opens out at the forward side, and is secured against an unintended release, in particular latched.

Within the scope of the invention, the handpiece body 2 may be formed in one piece. In the case of the exemplary embodiment it is formed in two pieces, transversely divided, having a rearward grip part 7 and, extending forwardly from its forward end, a cannula 8, whereby for the connection of the cannula 8 with the grip part 7 likewise a connection device 9, in particular a quick-release device, is provided. This can be formed by means of a plug-in fitting 11 having a plug-in recess 11a and an insertable plug-in pin 11b fitting therein. In the case of the exemplary embodiment, the plug-in recess 11a opens out in the region of a plane and transversely running end face 7a out of the grip part 7, and the plug-in pin 11b extends from the cannula 8 in the region of an end face 8a of the canula 8 parallel to the end face 7a. The plug-in recess 11a and the plug-in pin 11b are preferably formed to be circular or cylindrical or stepped cylindrical. Through this they form a rotary bearing 12 for the cannula 8 in which this is freely rotatably mounted. For axial securing of the cannula 8 in the plug-in fitting 11 there is provided a latching device 10 which upon manual plugging together self-actingly springs in and upon pulling apart self-actingly springs out, having for example one or two mutually oppositely lying latch noses 10a on spring arms 10b projecting rearwardly from the connection body 3b, whereby the latch noses 10a engage behind a preferably ring-like latch edge 10c and upon manual pulling apart spring out. Through this there is formed a turn/plug-in coupling having a latching device which can be manually overcome.

The functional handpiece has at least one media line 14 for a flowable medium, for example water or air or spray, which extends from the rear longitudinally through the functional handpiece 1 to a media nozzle 15 opening out in the light emission element 3 preferably at the end face and centrally. Thereby, the media line 14 passes through a preferably hollow cylindrical dividing joint 16, between the coupling parts 11a, 11b, in a Z-form. The radial medium line section passes through the dividing joint 16 in the region of a ring groove 17 which may be located in the inner surface of the plug-in recess 11a or in the outer surface of the plug-in pin 11b. Through this, with a circular cross-sectional form of the plug-in/turn coupling 13, there is ensured a rotatability of more than 360° with permanent throughflow of the medium through the coupling. The passage of the media line 14 through the dividing joint 16 is sealed by means of sealing rings 11c arranged to both sides in ring grooves of the recess 11a or of the pin 11b.

In the case of the exemplary embodiment two media lines 14a, 14b are formed in the above-described manner, namely one for water and one for air or for compressed air, which are brought together in the region of the media nozzle 15 and in functional operation form a spray which emerges out of the media nozzle 15 preferably forwardly.

The desired medium can switched on and switched off by means of a manual actuation of push buttons 20 which are arranged in the forward region of the grip section 7.

At the rearward end, the handpiece body 2 has a coupling element 2b with which it is connectable, in particular screw connectable, with a flexible supply line. For the releasable connection of the at least one media line 14 with associated media line sections in the supply line there is provided a line coupling element 14c.

The at least one media line 14 may extend in the cannula 8 as a channel or at least in sections as a tube or pipe. In the case of the exemplary embodiment, the cannula 8 is of a sleeve-shaped cannula jacket 18 in which there is fixedly placed and sealed off from the rear a cannula base 19 in the form a cylindrical plug-in pin 21 in a rearward plug-in recess 22 of the cannula jacket 18, for example by means of an O-ring 23 which sits in a ring groove, in particular of the plug-in pin 21, and seals the dividing joint. The cannula base 19 can be fixed in the cannula sleeve 18 for example by press-fitting, gluing or latching.

The media lines 14a, 14b, after their Z-shaped passage through the dividing joint, extend axially forwardly and they are connected with plug-in connection elements at the forward side of the cannula base 19, which are plugged together with the media hoses or pipes. These extend forwardly, whereby the water line extends in a central through-hole 25 in the light emission element 3 which in its rearward region is considerably greater in its cross-section than the water line 14a. The through-hole 25, or the ring channel formed thereby, between the light emission element 3 and the water line 14a tapers forwardly so that in the forward end region the through-hole 25 surrounds the water line 14a with a small ring gap 27. For centering the water line 14a, ending at a small spacing from the end face of the light emission element 3, there is provided in the middle region of the light emission element 3 a ring-form centering element 28 which is supported with its outer periphery on the inner surface of the through-hole 25 and with its inner periphery closely surrounds the water line 14a and thus centers it.

The air line 14b ends at a rearwardly directed spacing from the forward end of the water line 14a in the enlarged ring cross-section 25. In the case of the exemplary embodiment, the air line 14b opens into the ring chamber 31 present between the cannula jacket 18 than the water line 14a, which in the region of the forward end of the air line 14b is axially divided and sealed by means of a disc 32, so that the compressed air cannot enter into the rearward region of the annular chamber 31. The disc 32 is emplaced in a sealed manner and it is passed through in a sealed manner by the water line 14a and the air line 14b in one or two neighbouring holes 33. The air line 14b ends before the light emission element 3. The through-hole 25 adjoins to the annular chamber 31. The centering element 28 is permeable for the air by means of non-illustrated axis-parallel holes.

Behind the light emission element 3 there is arranged a light delivery device which emits light into the light emission element 3. In the case of the exemplary embodiment there is provided at least one light conductor which extends from the rear to the light emission element 3 and into which light is radiated from the rear. The light conductor 36 may begin at the rearward end of the cannula 8, here at the rearward end of the plug-in pin 11b. Its rearward end face 36c, preferably planar, is a light inlet surface. The light feed into the light conductor 36 may be effected by means of a lamp arranged in the grip section 7. There may, however, also be arranged a rearward light-delivering light conductor 36d in the grip part 7 extending up to the light conductor 36. It is of advantage to let the light conductor 36 end bluntly at the light emission element 3, here at the rear surface of the pin-like connection body 3b. In the case of the exemplary embodiment there are arranged two corresponding light conductors 36a, 36b lying next to one another. The cannula 8 and the head section 4 converge in their cross-sectional sizes, in the direction forwardly, preferably continuously.

The latching device 6b is manually releasable and it is thus possible to de-mount the light emission element 3 and to exchange it for another or new light emission element, for example if the emission surface is impaired, for example scratched, which when working together with a drill of a working handpiece can easily happen.

The latching device 6b has a latching nose 6d which upon plugging together of the latch parts self-actingly springs out into its latching position due to the force of a spring or due to its material elasticity, in which latching position it engages behind a latching edge 6e. In the case of the exemplary embodiment, the latching nose 6d is formed on a spring arm 6f arranged eccentrically on a connection body 3b and standing up rearwardly, which spring arm upon insertion of the connection body 3b, springs in and self-actingly springs out with the latching nose 6d when this reaches the region of an outwardly through-going latching hole 6g in the sleeve jacket 18, the forward inner edge of which forms the latching edge 6e. The form and size of the latching hole 6g is adapted to the form and size of the latching nose 6d with slight play for movement, so that the latching nose substantially fills the latching hole 6g. In the latching position, the latching noise 6d is externally accessible and it can be moved into its released position through the latching hole 6g, for example with a finger or finger nail. Opposite the spring arm 6f there may be provided a second arm 6f which improves the plug-in guiding.

For simplifying the release of the latching it is advantageous to form the latching nose 6d with an undercut 6h in its foot region, the undercut 6h extending up to a connection web 6i in the rearward region of the latching nose 6d. Through this, a springing in of the forward region of the latching nose 6d is made possible by means of bending in, through which the movement of the latching nose beyond the latching edge 6e is simplified.

With a two-part configuration of the cannula 8, with the cannula jacket 18 and the cannula base 19 it is advantageous to extend the cannula base 19 forwardly with a support arm 19a which creates a laterally or transversely directed support between these parts at a forwardly directed spacing a from the cannula base 19. This is in particular advantageous in the case of a relatively short plug-in fitting for the cannula base 19 with latching spring arms 10a.

In the case of the exemplary embodiment, the support arm 19a is formed in two parts with the cannula base 19 and attached to its forward end, for example in that a foot section 19b or flange is attached at the end face, for example by means of non-illustrated screws, gluing or welding. Thereby, the foot section 19b may be put in place in a recess 19c, for example pressed in.

An additional support is attained if the forward end of the support arm 19a bears on a step surface 19d of the cannula jacket 18. The support arm 19a can be formed in an angled shape with its foot section 19b, in order to create space for the light conductor or light conductors 36.

A switch for the switching on of the light is provided for example on the functional handpiece 1 or at a foot switch (not shown).

The individual parts of the functional handpiece 1, in particular the externally accessible parts, are of a material which is corrosion resistant also with regard to disinfectant or sterilization mediums, preferably of plastics and/or metal.

The invention claimed is:

1. Functional handpiece, comprising
   an elongate handpiece body having a rearward end with a connection element for connection with a flexible supply line,
   said handpiece having a forward end with a light emisson element of a light permeable material for illuminating a treatment site,
   said light emission element having an outlet opening for a fluid medium,
   the light emission element forming a forward region of the functional handpiece and being releasably connected to a remaining region of the functional handpiece, and the light emission element having a plug-in fitting, and the remaining region comprising a cannula, the light emission element releasably connected to the cannula, the cannula including a latching edge;

wherein the light emission element is connected to the remaining region of the functional handpiece by means of a latching device integral with the light emission element, the latching device including a latching nose integral with the light emission element, which can spring in radially inwardly and can self-actingly spring out behind the latching edge on the cannula; and a light conductor is disposed within the cannula and extends from a lamp through the cannula and butts against the light emission element within the cannula to emit light into the light emission element.

2. Functional handpiece according to claim 1, wherein for release, the latching nose can be sprung in through an externally accessible hole in the remaining region of the functional handpiece.

3. Functional handpiece according to claim 1, wherein an outer surface of the light emission element and an outer surface of the remaining region of the functional handpiece adjoining thereon steplessly transition into one another.

4. Functional handpiece according to claim 1, comprising a plug-in pin extending rearwardly from the light emission element, said plug-in pin sitting in a plug-in recess in the adjoining remaining region of the functional handpiece.

5. Functional handpiece according to claim 4, wherein the light emission element bears on the remaining region with a step surface tapering the plug-in pin.

6. Functional handpiece according to claim 1, wherein the latching nose is arranged on a rearwardly upstanding spring arm.

7. Functional handpiece according to claim 1, wherein the remaining region further comprises a grip part releasably connected to the cannula.

8. Functional handpiece according to claim 7, wherein the cannula is curved or angled to a side of the functional handpiece.

9. Functional handpiece according to claim 7, wherein the cannula is mounted rotatably around a longitudinal axis of the functional handpiece.

10. Functional handpiece according to claim 9, wherein the cannula is connected by means of a plug-in/turn coupling.

11. Functional handpiece according to claim 10, comprising at least one media line passing through a hollow cylindrical dividing joint of the plug-in/turn coupling in a Z-form or at least one light conductor passing axially through the plug-in/turn coupling and extending to the light emission element.

12. Functional handpiece according to claim 7, wherein said cannula is releasably connected with the grip part by means of a quick-release connection.

13. Functional handpiece of claim 1, wherein said fluid medium is water, air, or spray.

14. Functional handpiece comprising an elongate handpiece body having a rearward end with a connection element for connection to a flexible supply line, and a forward end with a light emission element of a light permeable material for illuminating a treatment site, the light emission element having an opening for a fluid medium, the light emission element forming a forward region of the functional handpiece and being releasably connected to the remaining region of the functional handpiece by means of a plug-in fitting having a latching device integral with the light emission element, the latching device having a latching nose integral with the light emission element, wherein the latching nose can self-actingly spring out into its latching position behind a latching edge on the remaining region, and for release is externally accessible through a hole in the remaining region;

wherein the light emission element can emit light both forwardly out an end portion of the light emission element and laterally out a side portion of the light emission element.

15. Functional handpiece of claim 14, wherein said fluid medium is water, air, or spray.

16. Functional handpiece according to claim 14, wherein the remaining portion comprises a cannula and a grip part, the light emission element being releasably connected to the cannula.

* * * * *